(12) United States Patent
Bischof et al.

(10) Patent No.: US 8,765,400 B2
(45) Date of Patent: Jul. 1, 2014

(54) METHOD FOR THE DETECTION OF ACID PRODUCTION BY CARIOGENIC BACTERIA

(75) Inventors: Manuela Bischof, Nendeln (LI); Carlo Bolis, Igis (CH); Urs Lendenmann, Grabs (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 321 days.

(21) Appl. No.: 13/181,054

(22) Filed: Jul. 12, 2011

(65) Prior Publication Data

US 2012/0015398 A1    Jan. 19, 2012

(30) Foreign Application Priority Data

Jul. 19, 2010   (EP) .................................... 10169983
Jul. 12, 2011   (EP) .................................... 11173695

(51) Int. Cl.
  *C12Q 1/14*      (2006.01)
  *C12Q 1/04*      (2006.01)
(52) U.S. Cl.
  USPC ............................................. 435/36; 435/34
(58) Field of Classification Search
  USPC .................................................... 435/36, 34
  See application file for complete search history.

(56) References Cited

U.S. PATENT DOCUMENTS

| | | | |
|---|---|---|---|
| 4,359,455 A * | 11/1982 | Nakamura et al. .............. | 435/34 |
| 2002/0182742 A1 | 12/2002 | Takagi et al. | |
| 2003/0113266 A1 | 6/2003 | Matsumoto | |
| 2009/0047691 A1 | 2/2009 | Huwig et al. | |

OTHER PUBLICATIONS

Gehring et al., "Turku sugars studies X, occurrence of polysaccharide-forming streptococci and ability of the mixed plaque microbiota to ferment various carbohydrates," Acta Ondontol Scand 34(6):329-343, 1976.*
Minah & Lösche, Infection and Immunity, 17: 43-54, 1977.
G. David, "CRT bacteria" Kariesrisikotext (online), Ivoclar Vivadent AG, Nov. 27, 2002, www.ivoclarvivadent.com.

* cited by examiner

*Primary Examiner* — Rosanne Kosson
(74) *Attorney, Agent, or Firm* — Ann M. Knab; Thad McMurray (57) ABSTRACT

The present invention relates to a method for the semi-quantitative determination of cariogenic bacteria in a sample of saliva and/or plaque, in which the microorganisms contained in a sample of plaque or saliva are brought into contact with a carbon source that is fermented to acid by the cariogenic bacteria. The microorganisms are then incubated under conditions which make possible selective acid formation by the cariogenic bacteria. The acid formation is then detected by determining the pH at least once within a period of 12 hours after adding the carbon source, wherein the cariogenic bacteria are determined semi-quantitatively in the sample by comparison of the pH with at least one reference value. In addition, the invention provides kits for carrying out such methods.

11 Claims, 3 Drawing Sheets

| carbon | S. mutans | S. sobrinus | S. ratus | S. cricetus | S. gordonii | S. anginus | S. mitis | S. salivarius | L. casei | L. fermentum | L. acidophilus | L. rhamnosus | L. plantarum | L. salivarius | L. brevis | L. paracasei ss paracasei | L. paracasei ss tolerans | L. delbrueckii | L. grasseri | P. aeruginosa | S. aureus | S. lentus | S. epidermidis | C. albicans |
|---|---|---|---|---|---|---|---|---|---|---|---|---|---|---|---|---|---|---|---|---|---|---|---|---|
| Glucose | B3-5-5 | A5-5-5 | B3-4-5 | A5-5-5 | A4-5-5 | A5-5-5 | B3-5-5 | A5-5-5 | A5-5-5 | B2-5-5 | B3-5-5 | B4-5-5 | A5-5-5 | A5-5-5 | C2-4-5 | A5-5-5 | A5-5-5 | A5-5-5 | A5-5-5 | D0-1-5 | B3-4-5 | B1-4-5 | B1-1-3 | A2-3-3 |
| Glucose 1%, Arginine 0.1-0.2% | B5-5-5 | B5-5-5 | | | C1-4-5 | | | B5-5-5 | B5-5-5 | B0-0-2 | | | | B3-5-5 | | | | | | | B2-4-5 | | | |
| Fructose | B2-4-5 | B5-5-5 | | | B3-3-4 | | B3-3-4 | A5-5-5 | A5-5-5 | B2-5-5 | G1 | A5-5-5 | | A4-5-5 | | | | | | | B2-4-5 | | | |
| Trehalose | C1-2-4 | C1-4-5 | | | | | A3-4-3 | | A5-5-5 | | | B3-5-5 | | | | | | | | | C1-2-3 | | | |
| Sucrose 1% | B2-4-5 | A5-5-5 | | | A3-5-5 | | B3-3-4 | A5-5-5 | | A2-4-5 | | | | | | | | | | neg. | B1-4-5 | D0-1-3 | B1-4-3 | C0-1-1 |
| Sucrose 20% | B3-5-5 | A5-5-5 | B3-5-5 | C1-4-4 | B2-4-4 | C1-1-3 | C1-2-4 | C1-1-2 | | B4-5-5 | neg. | F1 | F2 | D0-2-4 | neg. | neg. | neg. | neg. | | neg. | C1-2-5 | E0-0-2 | D0-1-3 | F1 |
| Sucrose 20%, Arginine 0.1% | B3-5-5 | B4-5-5 | F0-0-0 | C1-2-4 | E0-0-1 | E0-0-2 | C1-1-2 | D0-1-5 | neg. | B1-2-3 | E0-0-1 | F0-0-0 | C1-1-1 | C1-1-2 | | C1-1-1 | | | neg. | | D0-1-1 | E0-0-2 | E0-0-2 | F0-0-0 |
| Sucrose 20%, Asparagine 0.1% | B3-5-5 | C2-4-5 | | | D0-2-3 | | E0-0-3 | | neg. | | | | | | | | | | | | E0-0-2 | | | |
| Sucrose 20%, Serine 0.1% | B3-5-5 | C2-5-5 | | | C1-3-4 | | D0-1-3 | | neg. | | | | | | | | | | | | C1-4-5 | | | |
| Maltose 1% | B2-4-5 | B5-5-5 | | | B3-4-5 | | A2-3-3 | B5-5-5 | E0-0-1 | B1-2-4 | G1 | neg. | D0-1-1 | A3-5-5 | | B1-2-5 | | | | G1 | C1-2-4 | B1-1-2 | E0-0-1 | B1-2-3 |
| Maltose 20% | B3-5-5 | A3-5-5 | B1-2-4 | B1-4-5 | A4-4-3 | B3-4-4 | B1-3-4 | B1-2-2 | B1-1-2 | B2-2-4 | E0-0-1 | F0-0-0 | B1-2-5 | B1-3-5 | | B1-2-5 | | | | | B2-2-4 | | | B1-0-2 |
| Maltose 20%, Arginine 0.1-0.2% | B1-3-5 | B3-5-5 | F0-0-0 | E0-0-3 | F0-0-0 | C1-3-4 | F0-0-0 | | F0-0-0 | F0-0-0 | F0-0-0 | F0-0-0 | B1-2-5 | C1-3-5 | F4 | | | | | | E0-0-2 | | | C1-1-3 |
| Maltotriose | B2-4-5 | A5-5-5 | | | A2-4-5 | | A2-3-3 | C5-5-5 | neg. | A1-1-1 | D0-1-1 | A1-1-1 | D0-1-1 | | B2-4-4 | | | | | D0-1-5 | E0-0-1 | E0-0-1 | F2 | C1-1-2 |
| Raffinose (1-5) | E0-0-1 | neg. | B1-1-1 | F2 | C1-1-1 | | neg. | | neg. | A5-5-5 | D0-2-3 | neg. | D0-1-1 | A3-5-5 | F3 | D0-1-2 | neg. | neg. | | neg. | neg. | neg. | D0-1-1 | neg. |
| Inulin | D0-1-3 | E0-0-1 | | | C1-3-5 | | neg. | F5 | neg. | neg. | neg. | neg. | neg. | | | | | | | neg. | F1 | neg. | F1 | neg. |
| Aesculin 1% | E0-0-1 | neg. | | | E0-0-1 | | neg. | | neg. | G1 | neg. | neg. | neg. | | | | | | | neg. | neg. | neg. | neg. | neg. |
| Lactose | F0-0-0 | F0-0-0 | E0-0-1 | neg. | E0-0-1 | neg. | D0-1-3 | | C1-2-3 | A4-5-5 | C1-4-5 | D0-0-1 | C1-4-5 | A4-4-4 | F3 | B2-4-5 | E0-0-2 | neg. | A4-4-5 | neg. | B3-4-5 | neg. | neg. | neg. |
| Mannose | B1-2-3 | B3-5-5 | B2-4-4 | A4-4-4 | A2-3-4 | | B3-4-5 | | A5-5-5 | B4-5-5 | B5-5-5 | A5-5-5 | A5-5-5 | A5-5-5 | B2-4-4 | A5-5-5 | A5-5-5 | A5-5-5 | B2-3-5 | | C2-3-4 | | B1-4-3 | |
| Mannose 1%, Arginine 0.1% | | B3-5-5 | | | D0-2-4 | | D0-3-4 | | | neg. | B3-5-5 | B5-5-5 | B5-5-5 | F0-0-0 | | B5-5-5 | A5-6-5 | | | | | | | |
| Mannitol 1% | D0-1-2 | D0-2-2 | | | neg. | | neg. | | A1-2-2 | D0-2-3 | C1-2-3 | B2-4-5 | E0-0-2 | E0-0-2 | | D0-2-5 | C1-2-3 | neg. | C2-2-2 | | D0-1-2 | | | |
| N-Acetylglucosamin | F0-0-0 | E0-0-2 | E0-0-2 | E0-0-1 | D0-2-4 | E0-0-1 | C1-2-3 | neg. | A4-5-5 | neg. | C1-2-3 | A4-5-5 | A5-5-5 | A2-3-4 | | A5-5-5 | A5-5-5 | neg. | | | A1-1-1 | A5-5-5 | | A1-1-1 |
| D-Glucosamin | | neg. | | | E0-0-2 | | C1-2-3 | | | | neg. | C1-3-5 | B2-3-4 | D0-2-2 | | C1-3-5 | C1-3-5 | | C1-2-2 | | E0-0-2 | | | |
| Galactose 1% | F1 | neg. | | | neg. | neg. | E0-0-2 | | E0-0-1 | | neg. | E0-0-1 | | | | | | | | G1 | G0 | | | |
| Melezitose 1% | E0-0-1 | E0-0-2 | | | E0-0-1 | | neg. | | neg. | neg. | E0-0-1 | neg. | neg. | E0-0-2 | | neg. | neg. | neg. | B1-2-2 | | E0-0-2 | | | |
| Melibiose 1% | | neg. | | | neg. | | neg. | | neg. | | E0-0-2 | neg. | C2-2-4 | E0-0-2 | | neg. | neg. | A5-5-5 | B5-5-5 | | neg. | | | |
| Cellobiose 1% | | neg. | | | C5-5-5 | | E0-0-2 | | | | D0-2-5 | neg. | D0-2-2 | E0-0-2 | | neg. | neg. | B1-2-2 | B1-2-2 | | neg. | | | |
| L-Arabinose | | neg. | | | neg. | | neg. | | neg. | neg. | neg. | neg. | neg. | neg. | | neg. | neg. | neg. | C1-2-3 | | neg. | | | |
| Ribose 1% | | neg. | | | neg. | | neg. | | E0-0-1 | C2-2-2 | neg. | neg. | C2-2-3 | C2-2-2 | | C1-2-3 | neg. | | B5-5-5 | | neg. | | | |

| turnaround time | | colour level | Phenol red | Bromcresol purple |
|---|---|---|---|---|
| A | ≤15 min | 0 | dark red | violet |
| B | ≤30 min | 1 | red | bordeaux |
| C | ≤1 h | 2 | red-orange | red-brown |
| D | ≤2 h | 3 | orange | green-violet |
| E | 4 h | 4 | orange-yellow | dark yellow |
| F | ≤24 h | 5 | yellow | yellow |
| G | ≤72 h | | | |

METHOD FOR THE DETECTION OF ACID PRODUCTION BY CARIOGENIC BACTERIA

CROSS-REFERENCE TO RELATED APPLICATIONS

This application claims the benefit of European Application Serial Number 11173695.5, filed on Jul. 12, 2011 and European Application Serial Number 10169983.3, filed Jul. 19, 2010, each of which are hereby incorporated by reference in their entirety.

TECHNICAL FIELD

The present invention relates to a method for the semi-quantitative determination of cariogenic bacteria in a saliva and/or plaque sample, wherein the microorganisms contained in a plaque or saliva sample are brought into contact with a carbon source that is fermented to acid by the cariogenic bacteria. The microorganisms are then incubated under conditions which make possible selective acid formation by the cariogenic bacteria. The acid formation is then detected by determining the pH at least once within a period of 12 hours after addition of the carbon source, wherein the semi-quantitative determination of the cariogenic bacteria in the sample is performed by comparing the pH with at least one reference value. In addition, the invention provides kits for carrying out such methods.

BACKGROUND

The human oral cavity is usually colonized by more than 800 different germs which are in a natural equilibrium with one another. This microflora which substantially consists of bacteria, however, also comprises organisms which can damage the health of teeth. This relates in particular to bacteria that are able to metabolize carbohydrates from the diet to organic acids. The acid, in particular lactic acid, attacks the tooth enamel, which leads first to a demineralization of the tooth surface. Owing to continuous colonization of the demineralized sites, in the course of time, lesions result which can attack through the tooth enamel to the dentine and the pulp.

The majority of the lactic acid responsible for caries is due to the metabolic activity of "mutans streptococci"; this group includes the species *S. mutans*, *S. sobrinus*, *S. rattus* and *S. cricetus*. In addition, the group of the lactobacilli is of importance in this context. Whereas these bacteria, together with differing other bacterial species that colonize the oral cavity, are in a healthy state in a stable equilibrium, under special conditions increased multiplication of mutans streptococci can occur, as a result of which the risk of developing caries considerably increases. The acid formation caused by mutans streptococci leads to an acid environment that in turn increasingly promotes the growth of lactobacilli. An increased growth of lactobacilli is accompanied by a further lowering of the pH, owing to the acid production by lactobacilli, which promotes progress of the disorder.

It has been found that within a few minutes after supply of a sugar solution, the pH in the plaque falls greatly owing to the fermentative activity of the bacteria colonizing the oral cavity. However, it was found in a clinical study that plaque samples from children who had detectable caries, and plaque samples from caries-free children had a comparable potential of lowering of the pH in the oral cavity (Minah & Lösche, Infection and Immunity, 17: 43-54, 1977). This is an indication that, in the human oral cavity, in addition to streptococci and lactobacilli, there is a number of other microorganisms which, although they excrete acid as metabolic by-products, do not present a significant risk of caries. Consequently, measuring the entire acid production in saliva is unsuitable for determining the number of cariogenic bacteria and therefore the caries risk of a patient. Rather, this risk is decisively determined by the concentration of the mutans streptococci and lactobacilli.

The quantitative or semi-quantitative determination of mutans streptococci and/or lactobacilli in the plaque or saliva can give information on the caries risk of a patient. For this reason, test methods have been developed that provide an investigation of plaque or saliva samples with respect to the concentration of the germs by plating them out on selective nutrient media. For instance, the test system obtainable as CRT©, bacteria from Ivoclar Vivadent is based on the selective enrichment of mutans streptococci or lactobacilli from saliva samples on nutrient agar plates. Saliva samples are streaked onto respectively bacitracin-containing Mitis Salivarius agar (selective for streptococci) and in parallel thereto onto Rogosa agar (selective for lactobacilli). By enumerating the colonies formed on the agar plates after incubation for two to three days, a statement can be made on the respective caries risk of the patient. Similar systems are also available as Dentocult from Orion Diagnostics and as Caricult from OralBiotech.

However, culturing saliva samples on nutrient media is time-consuming. Customarily, the results cannot be assessed until about two to three days after plating out the saliva sample. It is therefore an object of the present invention to provide a method with which a statement can be made with respect to the number of cariogenic bacteria in a plaque or saliva sample reliably and reproducibly in a short time. The method should be able to be carried out without complex apparatus and the result should be available within a few hours, if possible.

SUMMARY

According to the invention the above object is achieved by the subject matter of the present patent claims. The present invention, in a first aspect, provides a method for the semi-quantitative determination of cariogenic bacteria in a plaque or saliva sample, wherein
(a) the microorganisms contained in a plaque or saliva sample are optionally concentrated;
(b) the microorganisms are brought into contact with a carbon source which is fermented to acid by the cariogenic bacteria;
(c) the microorganisms and the carbon source are incubated under conditions which make possible selective acid formation by the cariogenic bacteria;
(d) the pH is determined at least once within a period of 12 hours after addition of the carbon source;
wherein the semi-quantitative determination of the cariogenic bacteria in the sample is performed by comparing the pH determined in step (d) with one or more reference values. The reference value or the reference values was (were) determined in advance by using a known concentration of the corresponding cariogenic bacteria.

The above method is directed towards semi-quantitative determination of bacteria which, owing to their acid formation, contribute to the development of caries (cariogenic bacteria). Quantification or semi-quantification of these bacteria in the saliva or plaque therefore facilitates a statement on the risk of developing a caries. The method is based on a substantially selective acid formation by bacteria that are correlated with the development and/or progress of a caries. Other bacteria that are likewise part of the oral flora but have only a small or no influence on the development or the course of a caries, must, in contrast, be excluded as far as possible from the acid formation. Particularly preferred cariogenic bacteria that should be detected semi-quantitatively on the basis of their acid formation using the present method, are mutans streptococci and/or lactobacilli. For each of these groups of organisms, conditions are disclosed herein that facilitate an essentially selective acid formation.

DESCRIPTION OF THE DRAWINGS

Embodiments of the present invention will be more fully understood and appreciated by the following Detailed Description in conjunction with the accompanying drawings, in which.

DETAILED DESCRIPTION

The method of the present invention uses a plaque or saliva sample from an individual in which the number of the respective bacteria in the oral cavity is to be determined semi-quantitatively. Customarily, the individual will be a human, but the use of the method in the veterinary field is not excluded. The method can be carried out with humans of any desired age. However, in a particular aspect of the invention, it is preferred that the human individual is a child, preferably a child before completion of their third, fourth, fifth, sixth or seventh year. At this age the establishment of oral hygiene can be specifically matched to the respective risk to the child in order to prevent a caries effectively in this manner.

A saliva sample can be obtained using conventional methods. Customarily, the volume of the saliva sample is 0.5, 1, 2, 3, 4, 5, 6, 7, 8, 9, 10 or 15 ml. In a preferred embodiment, the saliva sample is a sample having a volume of 0.5-5 ml which is used undiluted in the method according to the invention. In a further preferred embodiment, the saliva sample is a concentrated sample, i.e. the solids that are present in the saliva, such as, e.g., bacterial cells, have been separated off from the liquid component of the saliva by filtration, centrifugation or like methods, and transferred into a smaller volume of liquid (e.g. buffer).

A plurality of methods and devices for obtaining saliva are known from the prior art. In a simple embodiment, the donor allows the saliva to drip from the oral cavity, wherein this saliva is collected in a suitable sample vessel. Alternatively thereto, the saliva can also be extracted from the oral cavity by suction using an aspirator. If relatively large volumes of saliva are desired for carrying out the method according to the invention, the saliva formation can be mechanically stimulated, preferably by chewing movements. For example, a paraffin pellet that, on being chewed, promotes saliva formation, can be administered to the donor. The saliva can be collected after about 0.5 to 5 minutes, e.g. after 2, 3, 4 or 5 minutes.

The saliva obtained from the donor can also be used diluted, if required, in the method of the present invention. Dilution of the saliva sample can be required, e.g., if, owing to an excessive viscosity of the saliva, concentration by means of filtration is not possible or requires too long a time period. If a dilution is advisable under the given conditions, water (e.g. sterile water) or a buffer customary in the field of microbiology can be used which does not significantly impair the following fermentation of the cariogenic bacteria. Suitable buffers are, e.g., tris buffer, HEPES buffer or phosphate buffer.

The method according to the invention can, in addition, also be carried out using plaque samples from the donor under examination. For this purpose, films are obtained from the tooth surface using a sterile brush or a spatula by abrasion and are transferred into a suitable sample vessel. The plaque sample can then be taken up in water or a suitable buffer, e.g. in tris buffer, HEPES buffer or phosphate buffer. The resulting bacterial suspension can then be used directly in the method according to the invention.

Depending on the cariogenic bacteria that are to be detected, in a first step of the method according to the invention, it can be necessary or expedient, before addition of the carbon source to the microorganisms, first to concentrate the microorganisms present in the plaque or saliva sample. Such a concentration can be achieved, for example, by means of centrifugation of the plaque or saliva sample obtained from the donor and subsequent resuspension of the solids present in the sample in a smaller volume of water or buffer (e.g. tris buffer, HEPES buffer or phosphate buffer). In this manner, several ml of saliva can be taken up in a volume of 500 µl or less buffer or water. In doing so, volumes of less than 400 µl, less than 300 µl, less than 200 µl, less than 100 µl, less than 50 µl, less than 25 µl, less than 20 µl, less than 15 µl, less than 10 µl, less than 5 µl or less than 1 µl can be used. The solids obtained after centrifugation can also be directly resuspended in a part of the supernatant.

The plaque or saliva sample obtained according to the invention can, in addition, also be concentrated by filtration. In this process filters can be used that are known from microbiological practice, e.g. membranes that are used for the sterile filtration of solutions. These filters have a pore size that is small enough to prevent the passage of bacteria from the saliva sample into the permeate. It must be noted that streptococci in salvia generally grow in the form of biofilms and consequently are present in a matrix of extracellular polysaccharides. For this reason, streptococci can also be effectively filtered out of the salvia using filters having a pore size of about 15 µm or more. Suitable filters for lactobacilli preferably have a pore size of less than 2 µm, less than 1 µm, less than 0.5 µm, less than 0.3 µm, e.g. less than 0.25 µm. In a particularly preferred embodiment according to the invention, the filter for use in concentrating the salvia sample has a pore size in the range of 0.2-0.22 µm. Filters having such small pore sizes require application of a pressure during filtration. If the filtration is carried out using a filter material which is arranged on an absorbent mat (see below) or is only mediated by gravity, then correspondingly larger pore volumes must be selected. Suitable pore sizes are in the range of 1-10 µm, preferably 2-8 µm.

For the filtration in the context of the present invention, filters are used that customarily consist of polymeric materials such as polypropylene (PP), polyvinylidene fluoride (PVDF), polytetrafluoroethylene (PTFE), polyether sulphone (PES), polyvinylpyrrolidone (PVP) or polyether ether ketone (PEEK). Filters made of nylon, cellulose, nitrocellulose or glass or quartz fibres are also frequently used in separating off bacterial cells from liquids. Suitable filters are obtainable from various manufacturers, e.g. from Sartorius AG (Gottingen, Germany), Millipore (Schwalbach, Germany), Whatman (Maidstone, UK) or Pall GmbH (Dreieich, Germany). A particularly preferred filter material is the glass fibre filter material 934-AH from Whatman.

In one embodiment of the present invention the filtration is carried out using a multilayer filter, preferably a double-layer filter. Thereby, the various filter membranes, each of which forms a layer of the multilayer filter, can have identical or different pore sizes. Preferably, the different layers differ with respect to their pore size, wherein the layer of the filter that first comes into contact with the saliva sample has a larger pore size than the filter layers arranged thereunder. By means of such an arrangement of filter membranes, a prefiltration can be achieved. For instance, in a double-layer filter, e.g. a first membrane with a pore size of 0.4-20 µm can be provided, beneath which a further membrane having a pore size of 0.2 µm is arranged. The surface of the membranes can, if required, be chemically modified, e.g. in order to modify the hydrophilic properties of the membrane.

The filtration can be performed, for example, using a syringe. In doing so, an attachment can be used which comprises a suitable filter, wherein the diluted or undiluted saliva sample is passed through the filter material, applying a slight pressure. In a further simple embodiment, an absorbent mat is arranged below the filter, which mat is in contact with the filter. When the diluted or undiluted saliva sample is dripped onto the filter, the solids contained in the sample, such as, e.g., the bacterial cells, accumulate on the filter material, whereas the aqueous component of the sample is passed into the absorbent mat. As absorbent mat, use can be made of, in particular, superabsorbent materials such as, e.g., the LUQUASORB polymers obtainable from BASF. Superabsorbent materials that are already in fleece form such as, e.g., LUQUAFLEECE from BASF, are particularly suitable. In order to facilitate application of the samples by dripping, templates can be used that are fabricated from plastic or perspex and facilitate the targeted dripping of the plaque or saliva sample. After filtration has been performed, the filter material can be separated from the absorbent mat for the subsequent steps.

The microorganisms remaining on the filter material, in particular the cariogenic bacteria, can be rinsed from the filter material before the incubation with the carbon source using a volume of a suitable liquid (e.g. water, tris buffer, HEPES buffer, phosphate buffer). In doing so, the volume used for detachment from the membrane is lower than the starting volume of the saliva sample. The volume of the bacterial suspension that is subsequently used for the incubation with the carbon source depends essentially on the respective format of the subsequent acid tests (see below). If, e.g. the incubation with the carbon source and/or the detection of acid formation is carried out in tubes or cuvettes (e.g. made of glass or plastic), the volume of the bacterial suspension can be several ml. If the incubation with the carbon source and/or detection of acid formation is carried out on a filter or a membrane (e.g. on one of the test strips described hereinafter), the volume of the bacterial suspension will generally be in the range from 0.5 to 2000 µl, e.g. at about 5, 10, 20, 50, 60, 70, 80, 90, 100, 150, 200, 250, 300, 350, 400, 450 or 500 µl.

In a particularly preferred embodiment of the invention, the microorganisms, in particular the cariogenic bacteria, are not removed from the filter material, but remain on the filter material used for the concentration and are brought into contact directly thereon with the carbon source and/or the corresponding test reagents, e.g. with a pH indicator, etc. The acid formation in this case can be detected after addition of the carbon source and the test reagents, e.g. directly on the basis of the change of a pH colour indicator on the filter material. Since the absorption capacity of the filters is generally limited, the carbon source and test reagents, depending on the filter used, are applied in small volumes to the filter, preferably in a volume of about 5, 10, 20, 50, 60, 70, 80, 90, 100, 150, 200, 250, 300, 350, 400, 450 or 500 µl. It is particularly preferred that the volume per unit filter area is in the range of about 0.1-15 µl per mm2 of filter material, preferably 0.5-10 µl per mm2 of filter material. The concentration of the test reagents will be adjusted to the volume respectively applied.

The concentration, e.g. by means of filtration, can be carried out at a temperature of 20-40° C., wherein it is generally carried out at room temperature (i.e. at about 20° C.), in particular when the method according to the invention is designed as a rapid test that enables determination of the respective organisms within a few hours (e.g. in the context of a dental examination). Since the cariogenic bacteria contained in the concentrated plaque or saliva sample shall be examined in the subsequent step with respect to their acid formation, it must be ensured that the time period between concentration and addition of the carbon source is not too long. This ensures that the bacteria contained in the concentrated sample remain viable and metabolically active. It is preferred that the concentrated cariogenic bacteria are used in the course of minutes in the subsequent examination of acid formation. Preferably, the examination of acid formation proceeds in the course of 1, 5, 10, 15, 20, 25, 30, 60 minutes after concentrating the saliva sample.

Concentrating the plaque or saliva sample is not an obligatory step of the method according to the invention. However, the use of a concentrated bacterial suspension has a significant effect on the total duration of the method up to evaluation. Concentrated samples permit semi-quantitative evaluation of the method already after a few hours, preferably in the course of less than three hours, less than two hours, less than one hour, e.g. within 50 minutes, within 40 minutes, or within 30 minutes or less. In a particularly preferred embodiment, the method is designed as a rapid test that allows semi-quantitative determination of the concentration of cariogenic bacteria in a saliva sample in the course of one hour. This allows such a determination already in the context of a single visit to the dentist.

In the next step of the method, the microorganisms contained in the diluted or undiluted plaque or saliva sample or the microorganisms contained in the bacterial suspension produced by concentration are brought into contact with a carbon source that can be fermented to acid by the cariogenic bacteria that are to be quantified. The method of the present invention is based on establishing conditions under which essentially only the cariogenic bacteria that are to be detected are able to form acid. Therefore it is particularly preferred to select a carbon source that can be utilized exclusively by the cariogenic bacteria that are to be quantified, or that can be fermented more rapidly to acid by these bacteria than by other microorganisms of the oral flora. If the method according to the invention is intended to be carried out, e.g., in the course of 1-2 hours, it can prove to be sufficient when the cariogenic bacteria that are to be quantified exhibit a detectable acid formation already within about one hour, whereas the acid formation in other bacteria present in the saliva sample does not start until 3 hours or later, i.e. at a time point at which the method is already completed.

In the context of the present invention, it has been observed that, under conditions that strongly favour acid formation by cariogenic bacteria, the rate of pH decrease, i.e. the decrease in pH per unit time, is correlated with the concentration of the respective cariogenic bacteria in the saliva sample. Therefore, under these conditions, measuring the pH at different time points after addition of the carbon source gives information on the number of risk-relevant cariogenic bacteria in the original plaque or saliva sample (see examples).

Cariogenic bacteria that are particularly suitable for risk assessment on the basis of the method according to the invention comprise the group of so-called "mutans streptococci", which comprises in turn the species *S. mutans, S. sobrinus, S. rattus* and *S. cricetus*. These streptococci are among the first microorganisms that newly colonize a cleaned tooth surface. In addition, they are able to form a polymeric slime from food residues and saliva components with which they adhere to the tooth surface. The biofilm formed by the streptococci is also called plaque. This is a structured film of living and dead microorganisms in a matrix of polysaccharides and glycoproteins. Plaque particularly readily accumulates in the recesses of the chewing surfaces, in the region between the teeth and at the edge of the gums. This biofilm also makes it possible for other bacteria to become established on the surface of the tooth.

Figure 1:
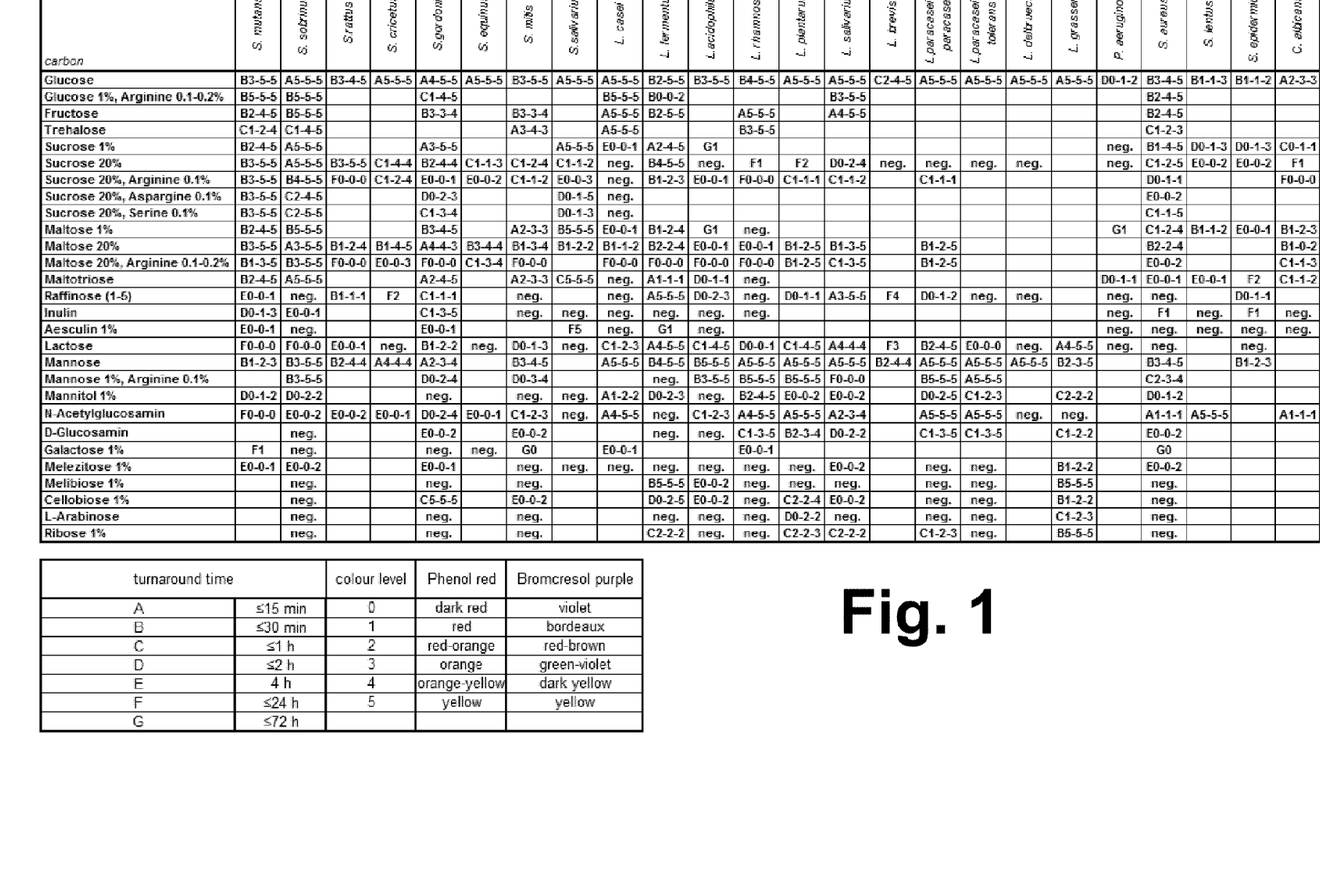
FIG. 1 shows the kinetics of acid formation by pure cultures. The letters A-G denote the time point at which acid production was first detected on the basis of a pH indicator. The numbers 0-5 give the stage of the pH reduction after 1, 2 and 4 h. The following coding thus applies: <time point of the colour change ><colour stage after 1 h><colour stage after 2 h><colour stage after 4 h >.

The number of mutans streptococci in a saliva sample is suitable, in a particular manner, for obtaining information on the caries risk. In one embodiment of the invention, the carbon source selected can be utilized by a plurality of or all of the abovementioned species of mutans streptococci, whereas other bacteria present in the saliva sample are not able, or are only able with a significant delay, to utilize the carbon source. Particularly preferred examples of such carbon sources are glucose, sucrose, maltose and maltotriose (or mixtures thereof), that are rapidly metabolized by all mutans streptococci. Although these sugars are also converted by other microorganisms in the saliva, they are converted significantly slower (see FIG. 1). In an alternative embodiment, the carbon source is utilized only by a single member of the group of the mutans streptococci, e.g. by *S. sobrinus* in the defined time window in which the method according to the invention is carried out. For instance, it can be seen from the table in FIG. 1, that when sucrose is used as carbon source at a concentration of 20% in the reaction batch, acid formation can only be detected with *S. sobrinus* within 15 minutes. If the method according to the invention is carried out using this carbon source, acid formation solely caused by this species could be detected if the method is ended after about 15-20 minutes, i.e. still before the sucrose is fermented by other cariogenic or non-cariogenic bacteria.

In an alternative embodiment of the present invention, the cariogenic bacteria that are to be quantified are the group of lactobacilli that comprises the species *L. acidophilus, L. casei, L. rhamnosus, L. brevis, L. plantarum* and *L. gasseri*. Bacteria of the genus Lactobacillus are capable of mixed acid fermentation and are responsible, furthermore, for the majority of the acid formed by microorganisms in the mouth. Lactobacilli are, in particular, able to colonize the biofilms formed by streptococci. At an active caries site, strains of the genus Lactobacillus may always be identified. For the abovementioned reasons, quantitative detection of bacteria of the genus Lactobacillus in saliva and plaque is also currently central to prevention-orientated practice and research. Carbon sources that can be used in order to detect selective acid formation by lactobacilli comprise, e.g., glucose, lactose, N-acetylglucosamine and mannose (or mixtures thereof).

The carbon source can be added to the reaction batch (consisting of the microorganisms of the saliva sample, the carbon source and the further optional components) in an amount of 0.05 to 60% by weight, e.g. in an amount of 0.1%, 0.5%, 1%, 2%, 3%, 4%, 5%, 6%, 7%, 8%, 9%, 10%, 15%, 20%, 30%, 40%, 50%, or more. For instance it has been found, that, e.g. by increasing the sucrose concentration in the test solutions, the specificity for certain mutans streptococci can be improved.

The contact between the cariogenic bacteria of the plaque or saliva sample and the selected carbon source can be made in a plurality of ways. For example, the carbon source can be present as a solution, e.g. dissolved in water or in a physiologically acceptable buffer. This solution can be mixed with a defined volume of a diluted, undiluted or concentrated liquid plaque or saliva sample. The carbon source, in addition, can also be used in the form of a powder or granules which are dissolved in the diluted, undiluted or concentrated liquid saliva sample. For instance, e.g. tubes, microtiter plates or cuvettes, can be provided that contain a defined amount of the carbon source in powder form, so that upon addition of a liquid saliva sample the contact between the cariogenic bacteria and the carbon source is established. Suitable carbon sources, such as e.g. mannose, are available in powder form from various providers.

In a preferred embodiment, the incubation with the carbon source and also the subsequent determination of the pH are carried out in a liquid reaction batch (solution or suspension). Depending on the volume of bacterial suspension and test reagents used in the method, tubes or cuvettes of glass or plastic, e.g. those having a volume of 5-10 ml, Eppendorf reaction tubes (with a volume of 1-2 ml) or microtiter plates can be used.

In a further preferred embodiment, the carbon source and/or the test reagents can be immobilized in dry form on a filter material, e.g. on the surface of a test strip. The test strips which can be used in this case are the filter materials mentioned above in connection with the concentration, i.e. filters whose pore size prevents transfer of cariogenic bacteria that are applied onto the filter material into the permeate. The diluted, undiluted or concentrated liquid saliva sample is applied dropwise to the filter material, whereby the immobilized carbon source is dissolved and thereby made accessible to the cariogenic bacteria. The utilization of the carbon source and the resultant acid formation can be detected directly on the filter material, e.g. by using a pH colour indicator. In a particularly preferred embodiment of the invention, the carbon source is maltose, maltotriose and/or sucrose that is present immobilized on a test strip. Such a test strip may be used for determining acid formation by mutans streptococci. In an alternative embodiment, the carbon source is lactose, N-acetylglucosamine and/or mannose, that is present immobilized on a test strip. Such a test strip may be used for determining acid formation by lactobacilli.

In a further particularly preferred embodiment, the material on which the carbon source and/or the test reagents are immobilized in dry form is the same material which was previously used for filtering the saliva sample for the purpose of concentrating the saliva sample. This means that the filter material is first used for enriching cariogenic bacteria from the saliva by filtering a saliva sample. In such an embodiment, however, it must be ensured that, in the filtration, the immobilized carbon source and/or the test reagents do not detach from the filter material, or only to a slight extent, since otherwise they would pass through the filter into the permeate and consequently would no longer be available for subsequent detection of the acid reaction on the filter. Only after completion of concentration of the plaque or saliva sample, a release of the carbon source and/or the test reagents on the filter should occur, so that the acid formation can take place on the filter material. This can be achieved, e.g., by means which ensure a time-delayed transfer of the immobilized reagents into solution. Thus it has proved to be advantageous to apply the carbon source and/or the test reagents (e.g. the colour indicator) in dry form to a filter material and to coat with a lacquer that causes delayed release.

In this case the quantitative ratios should be selected such that on the one hand sufficient carbon source and/or test reagents are present for acid formation by the cariogenic bacteria, but that on the other hand the filter will not be plugged. The release of the carbon source and/or the test reagents on the filter should take place only after 1-2 minutes, such that sufficient time remains before metabolization of the carbon source so as to facilitate enrichment of the bacteria by filtration of the saliva sample of the patient. In an optimum design of the test strip according to the invention, the carbon source and/or test reagents are released only after about 3-10 minutes, preferably about 5-8 minutes after application of the saliva sample. Thus, for example, 1-10 mg of the pulverized test reagents can be applied to a filter by means of suitable templates and fixed to the filter using 10-50 µl, preferably 20 µl, of a lacquer such as, e.g., 1% by weight of hydroxypropylcellulose. The filters can be dried in a drying cabinet and stored dry at room temperature until use.

Other lacquers suitable for fixing comprise polysaccharides such as, e.g., xanthan, chitosan, carrageenan; polyvinyl alcohols, such as, e.g., Poval from Kuraray; polyvinyl alcohol-PEG copolymers, such as, e.g., Kollicoat IR from BASF; polyvinylpyrrolidone, such as, e.g., Plasdone from ISP; vinylpyrrolidone-vinyl acetate copolymers, such as, e.g., Luviskol VA from BASF; alkyl esters of poly(methyl vinyl ether)maleic acid anhydride or maleic acid copolymers such as, e.g., Gantrez from ISP; polyvinylcaprolactams, such as, e.g., Luviskol Plus from BASF; acrylate copolymers, such as, e.g., Eudragit from Evonik or Luvimer 100P from BASF; poly(vinyl acetate-co-crotonic acid), such as, e.g., Luviset from BASF or Vinnapas from Wacker; vinylcaprolactam-vinylpyrrolidone-dimethylaminoalkyl methacrylate copolymers, such as, e.g., Advantage or Aquaflex from ISP; and polymers having quaternary ammonium compounds. Other suitable polymers for fixing the reagents to test strips comprise cellulose ethers such as, e.g., hydroxypropylcellulose, hydroxyethylcellulose, ethylhydroxyethylcellulose, hydroxypropylmethylcellulose and methylhydroxyethylcellulose. Furthermore, any combinations of the above compounds can be used.

After the microorganisms contained in the saliva sample have been brought into contact with the selected carbon source, they are incubated together with the carbon source under conditions that make possible an essentially selective acid formation by the cariogenic bacteria. In this connection, conditions suitable for the cariogenic bacteria in respect of temperature, pH and osmolarity are selected in which a particularly rapid metabolization of the carbon source by the bacteria can occur. If buffers are employed, these can be selected in such a manner that they provide a pH between 6.5 and 9, preferably between 6.5 and 8.5, wherein a pH between 7.0 and 8.5 is particularly preferred, e.g. 7.5. If the acid formation proceeds in the presence of a pH colour indicator, the pH must be set by using suitable buffers in such a manner that at the start of the incubation the pH of the solution is above the pKa of the indicator, so that when acid formation starts, a thorough colour change of the indicator is ensured. Thus, the pH of a solution in which the indicator phenol red is present lies in the region of about 8.5, since below this pH colour changes to a pH of about 5.0 are detectable (see Table 2).

The temperature of the incubation of the microorganisms with the carbon source can generally be between 20° C. and 60° C., preferably between 25° C. and 50° C., more preferably between 30° C. and 45° C. Acid formation generally proceeds most rapidly in a temperature range between 35° C. and 45° C.

According to the invention it is particularly preferred that the carbon source and/or the test reagents have a phosphate concentration between 1 mM and 10 mM, wherein 5 mM is particularly preferred, when a high test sensitivity is desired. On the basis of the buffer concentration used, the test sensitivity can also be reduced in order to be able to differentiate relatively high concentrations of cariogenic bacteria in the saliva. For grading the sensitivity, the concentration of the phosphate buffer can, e.g., be increased to >10 mM, >20 mM, >30 mM, >40 mM or even >50 mM. For buffering, other buffers can also be used, e.g., HEPES, MOPS, tris, etc. A further possibility for setting the sensitivity is to add slightly basic salts or polymers in the appropriate amount.

An increased selectivity in favour of cariogenic bacteria, especially mutans streptococci, can also be achieved by addition of amino acids and/or amino acid-containing polymers. Numerous acid generating bacteria in the oral cavity are able to enzymatically cleave the amino groups of amino acids. Thereby, the liberation of the basic amino group leads to a partial or full neutralisation of the acid which is produced by these bacteria. On the other hand, mutans streptococci, such as *S. mutans* and *S. sobrinus*, are not able to liberate the amino groups from amino acids to a noteworthy extent as these organisms usually lack the required enzyme. For example, neither *S. mutans* nor *S. sobrinus* has an arginine deiminase. Therefore, the addition of arginine is particularly suitable to counteract the acid production by bacteria which are not mutans streptococci (such as *S. gordonii, S. equinus, S. mitis, S. salivarius, L. casei* and *L. fermentum, S. aureus*).

Is the above depicted method for the semi-quantitative determination of cariogenic bacteria modified in that the microorganisms are incubated with the carbon source in the presence of an amino acid such as arginine and/or amino acid-containing polymers, the acid production of *S. mutans* and *S. sobrinus* will not be influenced whereas the acid production of other bacteria of the oral cavity will be suppressed by liberation of basic amino groups.

In a particularly preferred embodiment of the method of the invention, steps (b) and/or (c) therefore proceed in the presence of one or more amino acid(s) and/or one or more amino acid-containing polymer(s). Preferably, the amino acids are added to the reaction batch as free amino acids. Particularly preferred free amino acids which suppress the acid production of non-mutans streptococci comprise arginine, asparagine, glutamine, lysine and serine. The use of arginine as a free amino acid is particularly preferred. Alternatively, one or more amino acid-containing polymer(s) can also be added to the reaction batch. amino acid-containing polymers comprise short peptides (such as dipeptide, tripeptide, etc.) and polypeptides (with a length of, e.g. >10, >20, >30, >40, >50 or more amino acids). Mixtures of free amino acids with amino acid-containing polymers can also be used. A suitable mixture of free amino acids and amino acid-containing polymers which provide for an effective suppression of acid formation in non-mutans streptococci is, for example, peptone.

In a further preferred embodiment, glucose is used as carbon source in the above depicted method and the steps (b) and/or (c) will be carried out in the presence of an amino acid which is selected from the group consisting of arginine, asparagine, glutamine, lysine and serine, wherein the addition of arginine is particularly preferred.

able for the selective acid formation by mutans streptococci. Suitable antibiotics can be added to the carbon source and/or the test reagents in an amount of 0.01% by weight to 2% by weight, preferably in an amount of 0.1 to 1% by weight, e.g. 0.2% by weight. Particularly preferred antibiotics which inhibit the growth and/or the metabolic activity of bacteria of the genus lactobacillus are, e.g., vancomycin, clindamycin and nisin.

Table 1 shows the effects of adding antibiotics on the development over time of acid formation by various cariogenic and non-cariogenic bacteria that were incubated with 1% glucose in the presence of the indicator bromocresol purple. The exact composition of the test solutions is described in Table 3.

TABLE 1

Times taken for phenol red to completely turn yellow as a function of the antibiotic that was added to a glucose test solution.

| No. | Chemical addition | Conc. % | S. mutans | S. sobrinus | L. casei | L. rhamno-sus | S. mitis | S. aureus |
|---|---|---|---|---|---|---|---|---|
| 87 | None (Glucose 1%) | | 4 h | 2 h | 1 h | 1 h | 2 h | 4 h |
| 117 | Vancomycin | 0.5 | >24 h | >24 h | 2 h | 2 h | >24 h | 24 h |
| 119 | Clindamycin | 0.2 | >24 h | >24 h | 2 h | 2 h | 2 h | >24 h |
| 122 | Chloramphenicol | 0.2 | >24 h | 2 h | 1 h | 1 h | 2 h | 4 h |
| 124 | Clotrimazole | 0.2 | >24 h | 2 h | 1 h | 1 h | 1 h | 4 h |
| 126 | Metronidazole | 0.2 | 4 h | 2 h | 1 h | 1 h | 1 h | 4 h |
| 127 | Streptomycin | 0.2 | >24 h | 4 h | 2 h | 2 h | 2 h | 24 h |
| 129 | Neomycin | 0.2 | >24 h | >24 h | 2 h | 4 h | >24 h | 24 h |
| 130 | Kanamycin sulfate | 0.2 | >24 h | >24 h | 2 h | 4 h | >24 h | 24 h |
| 131 | Gentamicin sulfate | 0.2 | >24 h | >24 h | 2 h | 4 h | >24 h | 24 h |
| 143 | Nisin | 0.1 | 24 h | 24 h | 1 h | 1 h | >24 | >24 |

In above depicted method, the amino acid can be added in step (b) or (c). The amino acid can be added to the reaction batch, consisting of the saliva sample, the carbon source and additional optional components in an amount of 0.01 to 5% by weight, e.g. in an amount of 0.05%, 0.1%, 0.2%, 0.3%, 0.5%, 1%, 1.5%, 2%, 2.5%, 3%, 3.5%, 4%, 4.5%, or more. An amount of 0.1-0.2% by weight is particularly preferred. In case amino acid-containing polymers are used, the skilled person can readily determine suitable amounts of the respective polymers based on the above information.

An improved selectivity in favour of cariogenic bacteria, can also be achieved by the addition of urea. The addition of urea particularly provides for a suppression of acid formation by S. aureus. In the above described method steps (b) or (c) can, thus, also proceed in the presence of urea. In a particularly preferred embodiment sucrose is used as a carbon source in the above depicted methods, and steps (b) or (c) proceed in the presence of urea.

A further improvement of the selective acid formation can be achieved by adding antibiotics that are able to inhibit and/or stop the growth and/or metabolic activity of bacteria that are not to be quantified in the context of the method according to the invention, wherein the growth and/or acid formation of the cariogenic bacteria, in contrast, is not significantly impaired. For instance, for example by adding vancomycin, kanamycin or neomycin to the carbon source and/or the test reagents, particularly high specificity for lactobacilli may be achieved since these are scarcely inhibited by said antibiotics with respect to their growth or metabolic activity, whereas, e.g., streptococci and staphylococci are considerably inhibited. Similarly, by using bacitracin and metronidazole, conditions may be produced that are particularly suit- The incubation time which is selected for incubating the microorganisms with the carbon source selected according to the invention depends on the cariogenic bacteria that are to be quantified and also on the type and concentration of the carbon source. The incubation time is generally selected such that the strongest acid formation possible is achieved by the cariogenic bacteria that are to be quantified, whereas acid formation by non-cariogenic bacteria should be excluded as far as possible.

After incubation with the carbon source, the acid formation by the cariogenic bacteria is followed by determining the pH at least once within a time period of 12 hours after adding the carbon source. The time period in which the measurements are performed extends to a maximum of 12 hours after adding the carbon source, but it is preferred, however, that the time period is less than 10, 8, 6, 5, 4, 3, 2 or even less than one hour. Particular advantages of the method result when the time period in which the pH is measured and which therefore forms the time frame of the method comprises 0.25 to 3 hours. This makes possible determining the cariogenic bacteria and the associated caries risk in the context of a dental examination. It is further preferred that more than one pH measurement is made in the said time period. Preferably, in the time period, 2, 3, 4, 5, 6, 7, 8, 9, 10 or more measurements are performed. Thus, e.g., measurements can be performed in regular intervals of 5, 10 or 15 minutes over a period of 1, 2, 3 or 4 hours.

In carrying out the methods according to the invention, the presence of inhibitors of the enzyme carboxylic acid anhydrase, such as acetazolamid, methazolamid, dorzolamid and topiramate, results in an improvement with regard to the rate of the measurable acid generation.

Initially, after taking a saliva sample from an individual to be investigated, carbon dioxide will be liberated from the sample. Saliva contains hydrogen carbonate which reacts to carbon dioxide and water by taking up a proton. This reaction is catalyzed by the enzyme carboxylic acid anhydrase. The pH of the saliva sample will immediately after sampling increase from about 7.4 to about 8.0 or more by liberation of carbon dioxide. Initially, upon addition of an adequate carbon source to the sample and initiation of acid formation, the initial pH increase must be compensated, which will unnecessarily increase the reaction duration. Therefore, the addition of inhibitors of the enzyme carboxylic acid anhydrase, such as acetazolamid, methazolamid, dorzolamid and topiramate, to step (b) or (c) of the method of the invention can considerably decrease the duration of the complete method.

The inhibitor can be added to the reaction batch consisting of the microorganism of the saliva sample, the carbon source and the additional optional components in an amount of 0.01 to 5% by weight, such as in an amount of 0.05%, 0.1%, 0.2%, 0.3%, 0.5%, 1%, 1.5%, 2%, 2.5%, 3%, 3.5%, 4%, 4.5%, or more. An amount of 0.1% by weight is particularly preferred.

The pH can be determined in the abovementioned time period by means of a pH electrode. The use of a pH electrode requires that the microorganisms from the plaque or saliva sample are incubated with the carbon source in an aqueous solution. Since the rate of decrease, i.e. the decrease in pH with respect to a time unit, correlates under the above-described conditions with the concentration of the cariogenic bacteria in the sample, quantitative or semi-quantitative determination of the cariogenic bacteria in the initial sample can occur by comparing the measured pH with a reference value that was obtained in advance on the basis of a sample having a known number of the respective cariogenic bacteria at the same time point of the reaction and under the same conditions. Preferably, more than one measurement is performed, wherein for each time point at which a measurement is made, at least one corresponding reference value is available. For example, pH measurements can be performed in a time period of in total 4 hours after 1, 2, 3 and 4 hours (see examples). Customarily, for each of the defined time points at which the pH is measured, a plurality of reference values will be available that were obtained using known concentrations of the corresponding cariogenic bacteria. A high number of reference values that respectively reflect the pH at a defined time point after adding the carbon source for a determined concentration of the cariogenic bacteria facilitates a relatively exact quantitative or semi-quantitative determination of cariogenic bacteria in a sample of unknown concentration. For instance, the reference values in the determination of mutans streptococci can correspond, e.g., to concentrations of $10^3$ cfu, $10^4$ cfu, $10^5$ cfu and $10^6$ cfu.

In an alternative embodiment, the pH is determined using a pH indicator which changes colour on acid formation. The pH indicator is preferably added to the cariogenic bacteria together with the carbon source, e.g. by joint immobilization of pH indicator and carbon source on a test strip or by simultaneous addition of pH indicator and carbon source (preferably in the form of a single solution) to a diluted, undiluted or concentrated plaque or saliva sample. Various pH indicators have proved to be useful for carrying out the method according to the invention. These comprise, e.g., the indicators bromocresol purple, bromocresol green, m-cresol purple, bromothymol blue, phenol red and chlorophenol red. Table 2 shows the colour change of these indicators as a function of the pH. The incubation time that must be applied until a colour change can be detected, depends on the carbon sources and test reagents used and also on their absolute and relative quantitative ratios to one another. In a preferred embodiment, the time period to a colour change of the pH indicator is less than 60 minutes, less than 45 minutes, less than 30 minutes, less than 20 minutes or less than 15 minutes after mixing bacteria, carbon source and indicator.

The rate of the colour reaction can be controlled, inter alia, via the concentration of the buffer in the reaction batch. It has been found, for example, in solutions that contain the indicator phenol red that increasing the concentration of the phosphate buffer from 5 mM to 50 mM slowed the colour reaction by about the factor 3. By means of the buffer concentration, therefore, the sensitivity of this caries risk test can be set.

TABLE 2 pH indicators and colour thereof as a function of pH

| pK | m-Cresol purple 8.2 | Phenol red 7.9 | Bromothymol blue 7 | Bromocresol purple 6 | Chlorophenol red 5.6 | Bromocresol green 4.7 |
|---|---|---|---|---|---|---|
| 9.0-8.5 | violet | | | | | |
| 8.5-8.0 | brown | dark red | dark blue | | | |
| 8.0-7.5 | light brown | red | petrol blue | | | |
| 7.5-7.0 | dark yellow | red | greenish blue | violet | | |
| 7.0-6.5 | yellow | orange red | green | bordeaux | purple | |
| 6.5-6.0 | | orange | greenish yellow | reddish-brown | violett | |
| 6.0-5.5 | | orange yellow | yellow | greenish-violet | red | dark blue |
| 5.5-5.0 | | yellow | | dark yellow | orange | petrol blue |
| 5.0-4.5 | | | | yellow | orange | greenish blue |
| 4.5-4.0 | | | | | yellow | green |
| 4.0-3.5 | | | | | | greenish yellow |
| 3.5-3.0 | | | | | | yellow |

The colour change caused by the indicator is compared with a colour standard that was obtained in advance under identical conditions using samples that contained a known number of the respective cariogenic bacteria. This comparison with the colour standard allows semi-quantitative determination of cariogenic bacteria in the original sample. It is particularly preferred, in turn, that the colour standard is multistage, i.e. it comprises, for each of the defined time points at which the pH measurement was performed, a plurality of shades which may be assigned to a defined concentration of the cariogenic bacteria in the original saliva sample. Preferably, the colour standard is one in which the differences with respect to concentration may be recognized with the naked eye, i.e. without technical devices. The individual stages of the standard can be, e.g., logarithms to base ten of the concentration of the bacteria, wherein the concentration is measured in colony-forming units (cfu). Thus, e.g., the colour standard, by means of which the concentration of the mutans streptococci may be assessed, can comprise four stages which correspond to concentrations of $10^3$ cfu, $10^4$ cfu, $10^5$ cfu and $10^6$ cfu. The colour change obtained in the test method according to the invention can be compared with the four pre-given colour intensities. Generally, a statement on the concentration of the cariogenic bacteria in the plaque or saliva sample examined may be obtained thereby; e.g. it can be stated that the colour intensity obtained in the context of the test is due to a concentration of mutans streptococci in the range between $10^4$ and $10^5$ cfu. This indicates a high risk of caries.

In a further aspect, the invention also relates to a test strip for carrying out a method as described above, wherein, on the surface of the test strip, at least one carbon source and one pH indicator were immobilized in such a manner that, on contacting the test strip with a bacterial suspension, they are released from the test strip and dissolve in the liquid bacterial suspension. The carbon source is selected as described above in such a manner that it is fermented to acid selectively by cariogenic bacteria such as, e.g., mutans streptococci or lactobacilli. The pH indicator is able to change colour on acid formation, wherein the change is preferably perceivable with the naked eye. It is sufficient that the test strip comprises one of the two mentioned components in immobilized form. The other respective component can be added to the test strip, e.g. by dripping. In a preferred embodiment, both the carbon source and also the indicator are immobilized on the surface of the test strip. The carbon source and/or the pH indicator can be immobilized on the test strip by means of a lacquer (see above).

The test strip preferably further comprises a filter material (or consists thereof) having a pore size in the range 1-10 μm. Preferred pore sizes are in the range of 2-8 μm, e.g. 2, 3, 4, 5, 6, 7 or 8 μm. The carbon source and/or the pH indicator are immobilized on this filter material. This has the advantage that the filter material can be used directly for enrichment of the cariogenic bacteria.

The invention also relates to a test kit for carrying out a method as described above, comprising:
(a) a carbon source which is fermented to acid by the group of cariogenic bacteria;
(b) a pH indicator which changes colour on acid formation;
(c) a colour standard which facilitates the semi-quantitative determination of the concentration of the cariogenic bacteria in the sample.

Preferably, the colour standard is a multistage standard as described above that acts as a reference. In addition, the kit can comprise instructions for carrying out the method. The kit can of course also comprise one or more of the test strips as described above.

EXAMPLES

Bacterial Strains

Stock cultures of the strain selected for the experiments were stored on CRYOBANK (Mast Diagnostica, CRYO/M) ceramic supports at a temperature of −80° C. For culturing, a ceramic ring was placed into 10 ml of nutrient medium and incubated 14-72 h. This culture was designated passage 0 (P0). Then, 100 μl of culture were inoculated into 10 ml of fresh medium and incubated for 24 h. Cultures of passage 2 were used for the subsequent experiments on acid production. The cultures were diluted in this case until an absorption at 650 nm of about 0.6-1.0 was obtained. The bacterial suspensions were centrifuged at 8000 rpm for 5 minutes. The culture supernatant was removed and the pellet was resuspended in the same volume of water (10 ml, deionized, sterile). The sample was centrifuged again (8000 rpm, 5 minutes) and the supernatant was removed. The pellet was subsequently resuspended in 1 ml of deionized water which corresponds to 1/10 of the original volume.

Acid Production in vitro

For measuring the acid production, 40 μl of bacterial suspension were added to 100 μl of a test solution in 96-well polystyrene microtiter plates or in 1.5 ml microcentrifuge tubes, which test solution contained, in addition to a suitable pH indicator (e.g. phenol red and bromocresol purple) a fermentable carbon source, 5 mM of phosphate or 5 mM of tris-HCl and optionally an antibiotic or an amino acid, such as arginine. The test solutions used were adjusted to a defined starting pH. In the production of the test solutions, the components were dissolved in 75% of the desired end volume of deionized water. Then, the appropriate pH was adjusted and the mixture was filled up to the calculated volume using deionized water. The solutions produced were stored in a refrigerator and used after no longer than 2 weeks.

After addition of the bacterial suspension to the respective test solution, the colour change of the pH indicator was assessed visually against a reference sample (only test solution) at regular intervals. In between, the samples were stored in the incubator at 37° C. The acid formation was described visually (without support by optical measuring devices) by the colour changes of the test solutions. The results of the studies are listed in the table shown in FIG. 1.

The composition of the test solutions used in the context of the present invention is described in Table 3 below.

TABLE 3

| Compositions of the test solutions. | | | | | | |
|---|---|---|---|---|---|---|
| No. | Indicator | Substrate | Conc. (%) | Additions | Buffer | pH |
| 87 | Phenol red | Glucose | 1 | | Phosphate, 5 mM | 8.5 |
| 98 | Bromcresol purple | Lactose | 1 | | Phosphate, 5 mM | 7.3 |
| 117 | Phenol red | Glucose | 1 | Vancomycin, 0.5% | Phosphate, 5 mM | 8.5 |
| 119 | Phenol red | Glucose | 1 | Clindamycin, 0.2% | Phosphate, 5 mM | 8.5 |
| 122 | Phenol red | Glucose | 1 | Chloramphenicol, 0.2% | Phosphate, 5 mM | 8.5 |

TABLE 3-continued

Compositions of the test solutions.

| No. | Indicator | Substrate | Conc. (%) | Additions | Buffer | pH |
|---|---|---|---|---|---|---|
| 124 | Phenol red | Glucose | 1 | Clotrimazole, 0.2% | Phosphate, 5 mM | 8.5 |
| 126 | Phenol red | Glucose | 1 | Metronid-azole, 0.2% | Phosphate, 5 mM | 8.5 |
| 127 | Phenol red | Glucose | 1 | Streptomycin, 0.2% | Phosphate, 5 mM | 8.5 |
| 129 | Phenol red | Glucose | 1 | Neomycin, 0.2% | Phosphate, 5 mM | 8.5 |
| 130 | Phenol red | Glucose | 1 | Kanamycin sulfate, 0.2% | phosphate, 5 mM | 8.5 |
| 131 | Phenol red | Glucose | 1 | Gentamycin sulfate, 0.2% | Phosphate, 5 mM | 8.5 |
| 136 | Phenol red | Sucrose | 20 |  | Phosphate, 5 mM | 8.5 |
| 143 | Phenol red | Glucose | 1 | Nisin, 0.1% | Phosphate, 5 mM | 8.5 |
| 209 | Phenol red | Sucrose | 20 |  | Phosphate, 50 mM | 8.5 |
| 237 | Phenol red | Sucrose | 20 | Arginine 0.1% | Phosphate, 5 mM | 8.5 |
| 323 | Phenol red | Maltose | 20 |  | Phosphate, 5 mM | 8.5 |
| 337 | Phenol red | Sucrose | 20 | Urea 0.1% | Phosphate, 5 mM | 8.5 |
| 344 | Phenol red | Maltose | 20 | Arginine 0.1% | Phosphate, 5 mM | 8.5 |
| 354 | Phenol red | Sucrose | 20 | Aspargine 0.1% | Phosphate, 5 mM | 8.5 |
| 355 | Phenol red | Sucrose | 20 | Lysine 0.1% | Phosphate, 5 mM | 8.5 |
| 358 | Phenol red | Sucrose | 20 | Serine 0.1% | Phosphate, 5 mM | 8.5 |
| 408 | Phenol red | Sucrose | 20 | Glutamine 0.1% | Phosphate, 5 mM | 8.5 |
| 409 | Phenol red | Glucose | 1 | Arginine 0.1% | Phosphate, 5 mM | 8.5 |
| 410 | Phenol red | Glucose | 1 | Aspargine 0.1% | Phosphate, 5 mM | 8.5 |
| 411 | Phenol red | Glucose | 1 | Glutamine 0.1% | Phosphate, 5 mM | 8.5 |
| 412 | Phenol red | Glucose | 1 | Serine 0.1% | Phosphate, 5 mM | 8.5 |
| 413 | Phenol red | Glucose | 1 | Urea 0.1% | Phosphate, 5 mM | 8.5 |

Additionally, it was tested as described above which influence the addition of amino acids or urea has on the time span in which the indicator phenol red will completely change to yellow (see the following Table 4).

TABLE 4

Time until Phenol red has completely turned yellow when amino acids are added to the carbon sources.

| No. | carbon | addition | S. mutans | S. sobrinus | S. gordonii | L. fermentum | S. aureus |
|---|---|---|---|---|---|---|---|
| 136 | Sucrose 20% |  | 2 h | 1 h | 2 h | 3 h | 4 h |
| 355 | Sucrose 20% | Lysine 0.1% | 2 h | 4 h | 24 h | nd | 24 h |
| 237 | Sucrose 20% | Arginine 0.1% | 2 h | 2 h | 24 h | >24 h | >24 h |
| 354 | Sucrose 20% | Aspargine 0.1% | 2 h | 4 h | >24 h | >24 h | >24 h |
| 408 | Sucrose 20% | Glutamine 0.1% | 2 h | 4 h | >24 h | >24 h | 24 h |
| 358 | Sucrose 20% | Serine 0.1% | 2 h | 2 h | 4 h | >24 h | 24 h |
| 337 | Sucrose 20% | Urea 0.1% | 1 h | 1 h | 4 h | 2 h | 24 h |
| 87 | Glucose 1% |  | 1 h | 1 h | 2 h | 3 h | 2 h |
| 409 | Glucose 1% | Arginine 0.1% | 1 h | 1 h | >24 h | 24 h | 4 h |
| 410 | Glucose 1% | Aspargine 0.1% | 2 h | 1 h | 4 h | >24 h | 4 h |
| 411 | Glucose 1% | Glutamine 0.1% | 2 h | 1 h | 4 h | 24 h | 4 h |
| 412 | Glucose 1% | Serine 0.1% | 2 h | 1 h | 4 h | 24 h | 4 h |
| 413 | Glucose 1% | Urea 0.1% | 1 h | 1 h | 4 h | 2 h | 2 h | nd: no data.

Clinical Investigations with Saliva Samples

To investigate whether semi-quantitative determination of cariogenic bacteria in a saliva sample according to the method of the present invention correlates with the results of the proven caries risk test CRT©bacteria, approximately 80 saliva samples were studied in parallel using the CRT©bacteria test and the test solutions 136 and 98 of the present invention (see Table 3).

The test persons were instructed to chew a paraffin pellet (CRT, Ivoclar Vivadent AG, Schaan, Liechtenstein) for 30 seconds and to spit out the stimulated saliva. The persons were then instructed to chew on the paraffin pellet for a further 5 minutes and the saliva was collected in a 50 ml plastic tube having a screw lid. The CRT©bacteria test permits the parallel semi-quantitative detection of mutans streptococci and lactobacilli present in the saliva and classification of the subject into one of four different risk stages. The test was carried out as follows.

1. Remove the agar support from the sample tube.
2. Place an $NaHCO_3$ tablet on the bottom of the tube.
3. Carefully take off protective films from both agar surfaces; do not touch agar surfaces in the course of this.
4. Wet completely each agar surface with 50 μl of saliva using a pipette without scratching the agar surface.
5. Drain off excess saliva by dripping.
6. Return the agar support into the tube and close tightly.
7. Store the tube upright for 48-72 hours at 37° C. in the incubation cabinet, e.g. Cultura/Ivoclar Vivadent.
8. After removing the tube from the incubation cabinet, compare the colony density of the mutans streptococci or lactobacilli in each case with the corresponding pictures of the accompanying standards.

Classification was performed into stages CRT 0-1 (corresponding to about $10^3$ cfu), CRT 1-2 (corresponding to about $10^4$ cfu), CRT 2-3 (corresponding to about $10^5$ cfu) and CRT 3 (corresponding to about $10^5$ cfu). Aliquots in each case of 50 μl of the same saliva samples were then incubated with 50 μl of test solution 136 (for mutans streptococci) or test solution 98 (for lactobacilli) and the pH was measured in each case 1, 2, 3 and 4 hours after addition of the carbon source to the samples, using a pH electrode or on the basis of the colour change of the indicator. The results are summarized hereinafter.

|  | pH with test solution 136 | | | |
|---|---|---|---|---|
|  | 1 h | 2 h | 3 h | 4 h |
| CRT 0-1 | 7.2 | 6.9 | 6.6 | 6.2 |
| CRT 1-2 | 7 | 6.7 | 6.3 | 6 |
| CRT 2-3 | 6.9 | 6.5 | 5.9 | 5.7 |
| CRT 3 | 6.8 | 6 | 5.5 | <5.5 |

|  | pH with test solution 98 | | | |
|---|---|---|---|---|
|  | 1 h | 2 h | 3 h | 4 h |
| CRT 0-1 | 7.2 | 7 | 6.8 | 6.5 |
| CRT 1-2 | 7.1 | 6.8 | 6.5 | 6 |
| CRT 2-3 | 7 | 6.5 | 6 | 5.5 |
| CRT 3 | 6.8 | 6 | 5.5 | 5 |

Figure 2:
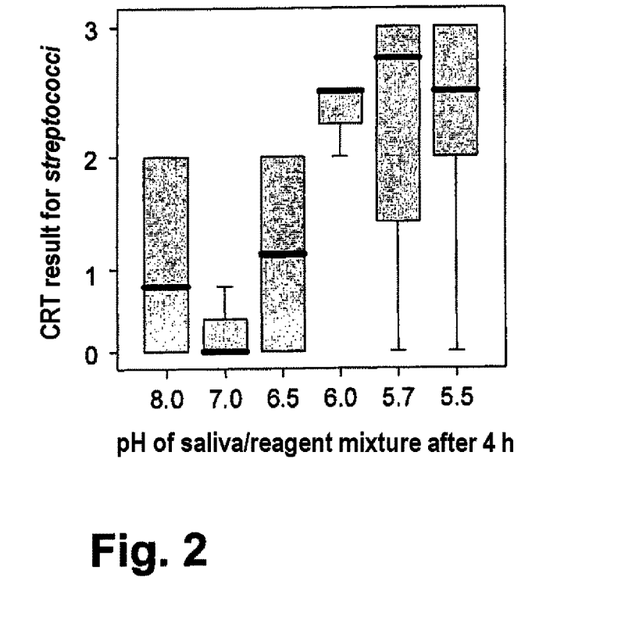
FIG. 2 shows the correlation between the results of CRT bacteria and the method according to the invention using test solution No. 136 after 4 h for mutans streptococci. It can be seen that the risk threshold of $>10^5$ cfu/ml corresponds to a pH reduction to below about 6.5.
Figure 3:
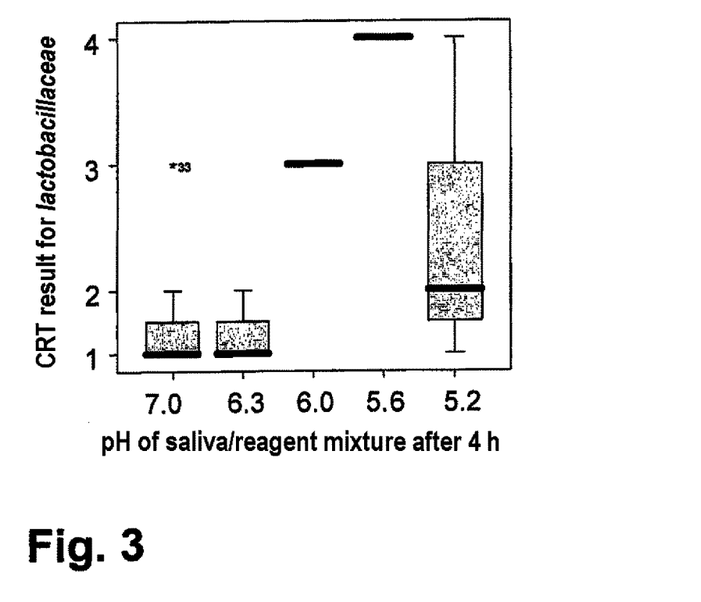
FIG. 3 shows the correlation between the results of CRT bacteria and the method according to the invention using test solution No. 98 after 4 h for lactobacilli. It can be seen that the risk threshold of $>10^5$ cfu/ml corresponds to a pH reduction to below about 6.0.

It was found that the correlation between the CRT bacteria and the measured pHs was statistically significant (see FIGS. 2 and 3).

To test whether the semi-quantitative determination of cariogenic bacteria in a saliva sample according to the method of the present invention will correlate with the results of the established caries risk test CRT© bacteria in children as well as in adults, 70 saliva samples of adults and 111 saliva samples of children were investigated with the test variants 136 and 323 for mutans streptococci and the test variant 98 for lactobacilli and the test solutions according to the present invention.

Figure 4:
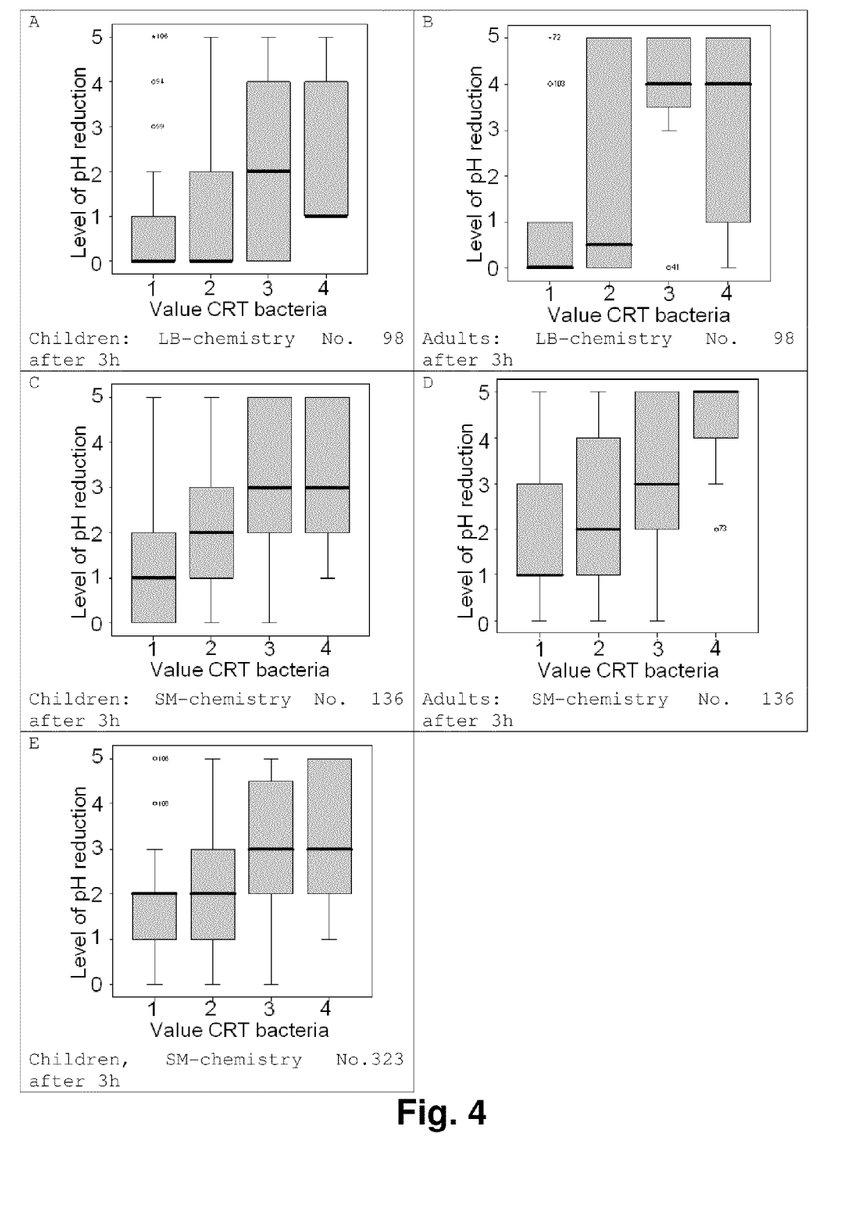
FIG. 4 shows the correlation between the results of CRT bacteria and the method according to the invention using (A, B) test solution no. 98, (C, D) test solution no. 136 or (E) test solution no. 323 in (A, C, E) children and (B, C) adults after 3 hours for (A, B) lactobacilli and (C, D) mutans streptococci. The numbers 0-5 on the Y-axis show the level of the pH reduction (compare FIG. 1). It is apparent that the levels of pH reduction increase with increasing CRT bacteria value (X-axis).

The CRT© bacteria test and the corresponding classification in levels was done as described above (compare "Clinical investigations with saliva samples"). After carrying out the CRT© bacteria test aliquots of the same saliva samples were subsequently incubated 1:1 with test solution 136 or 323 (for mutans streptococci) and test solution 98 (for lactobacilli) respectively, and the pH value was measured 3 hours after addition of the carbon source to the samples with the help of the colour change of the indicator. The results are depicted in FIG. 4. It is apparent that the levels of the acid formation in saliva samples with the test solution 98 correlate with the CRT© bacteria values for lactobacilli (FIG. 4A, 4B) Likewise, the levels of acid formation of saliva samples with test solution 136 (FIG. 4C, 4D) and 323 (FIG. 4E) correlate with the results obtained from the CRT©, bacteria test for mutans streptococci.

The results of the statistical analyses are summarized in the below table 5.

TABLE 5

Statistical analysis of the correlation of CRT bacteria and different test solutions according to Spearman rank correlation coefficient (Spearman rho) (N = sample size, p = probability that result is random)

|  | adults | | | children | | |
|---|---|---|---|---|---|---|
|  | N | correlation | p | N | correlation | p |
| SM 136, 3 h | 69 | 0.51 | <0.001 | 110 | 0.40 | <0.001 |
| SM 323, 3 h |  | not testet |  | 110 | 0.37 | <0.001 |
| LB 98, 3 h | 70 | 0.36 | 0.002 | 111 | 0.28 | 0.003 |

Investigations of the Concentration of Saliva Samples

To control whether the time needed for one test can be shortened by concentrating the saliva samples by passive filtration, the detection of mutans streptococci in nine concentrated and nine non-concentrated saliva samples was compared. For this purpose, holes with a diameter of 5 mm were drilled into a plastic disc. These holes were sealed with a filter material (glas fibre) from below. Discs and filter were placed onto a suction-fleece (cellulose) in such a manner that the filter was arranged between the plastic disc and the suction-fleece. 60 μl of the saliva sample were added through one of the holes onto the filter. Subsequently, 20 μl of test solution 136 were added to the filter. After completion of filtration, the suction-fleece was separated from the disc with the filters, and the plastic disc and the filters were incubated for up to 4 h at 37° C.

For the purpose of comparison, 60 μl saliva was mixed with 60 μl test solution 136 in microtitre plates and incubated for up to 24 h at 37° C. In the plastic discs as well as in the microtitre plates, the level of pH reduction was measured by means of the colour change of the indicator after an incubation time of 30, 45, 60, 120 and 180 min. Both methods were compared with each other as well as with the CRT©, bacteria test (CRT SM) (compare colour nuances from 0-5 in the below table).

|  | filter stencils | | microtiter plates | |
|---|---|---|---|---|
| CRT SM | 30 min | 45 min | 120 min | 180 min |
| 3 | 3 | 5 | 5 | 5 |
| 3 | 5 | 5 | 5 | 5 |
| 0 | 1 | 1 | 2 | 5 |
| 0 | 1 | 2 | 2 | 3 |
| 3 | 3 | 3 | 2 | 4 |
| 2 | 3 | 4 | 5 | 4 |
| 2 | 3 | 4 | 3 | 5 |
| 1 | 1 | 2 | 1 | 1 |
| 0 | 1 | 2 | 1 | 1 |

The depicted changes in colour correlate with the measured CRT values. Additionally, it could be shown that after concentrating the saliva samples through a filter, a colour change comparable to that in microtitre plates after 120 min will occur after 45 min. Therefore, the above described concentration of the samples allows the performance of the method of the invention in a considerably shorter time.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A method for the semi-quantitative determination of cariogenic bacteria in a plaque or saliva sample, in which
    (a) the microorganisms contained in a plaque or saliva sample are optionally concentrated;
    (b) the microorganisms are brought into contact with a carbon source which is fermented to acid by the cariogenic bacteria;
    (c) the microorganisms and the carbon source are incubated under conditions which facilitate selective acid formation by the cariogenic bacteria;
    (d) the pH is determined at least once within a period of 12 hours after addition of the carbon source;
    wherein the semi-quantitative determination of the cariogenic bacteria in the sample is performed by comparing the pH determined in step (d) with at least one reference value, and wherein the cariogenic bacteria are Streptococcus mutans and wherein the carbon source is maltotriose.

2. Method according to claim 1, wherein the pH is determined in step (d) with a pH electrode.

3. The method according to claim 1, wherein the pH is determined in step (d) using a pH indicator that changes its colour on acid formation.

4. The method according to claim 3, wherein the pH indicator is selected from the group consisting of bromocresol purple, bromocresol green, m-cresol purple, bromothymol blue, phenol red and chlorophenol red.

5. Method according to claim 1, wherein step (c) proceeds in the presence of one or more antibiotics that do not significantly impair the growth and/or the acid formation of the cariogenic bacteria.

6. The method according to claim 1, wherein steps (b) and/or (c) proceed in the presence of one or more amino acid(s) and/or one or more amino acid-containing polymer(s).

7. The method according to claim 6, wherein steps (b) and/or (c) proceed in the presence of one or more amino acid(s) selected from the group consisting of arginine, asparagine, glutamine, lysine and serine.

8. The method according to claim 7, wherein steps (b) and/or (c) proceed in the presence of arginine.

9. The method according to claim 1, wherein the cariogenic bacteria further comprise Lactobacilli.

10. Method according to claim 9, wherein step (c) proceeds in the presence of one or more antibiotics selected from the group consisting of vancomycin, clindamycin and nisin.

11. Method according to claim 9, wherein the carbon source that is fermented to acid by the lactobacilli is selected from the group consisting of mannose, lactose and N-acetyl-glucosamine.

* * * * *